United States Patent [19]

Eisenberg et al.

[11] Patent Number: 5,436,850
[45] Date of Patent: Jul. 25, 1995

[54] METHOD TO IDENTIFY PROTEIN SEQUENCES THAT FOLD INTO A KNOWN THREE-DIMENSIONAL STRUCTURE

[75] Inventors: David Eisenberg, Los Angeles; James U. Bowie, Culver City; Roland Luthy, Los Angeles, all of Calif.

[73] Assignee: The Regents of the University of California, Oakland, Calif.

[21] Appl. No.: 218,685

[22] Filed: Mar. 28, 1994

Related U.S. Application Data

[63] Continuation of Ser. No. 728,640, Jul. 11, 1991, abandoned.

[51] Int. Cl.$^6$ .................... G06F 19/00; C12Q 1/68
[52] U.S. Cl. .................... 364/496; 364/497; 436/89; 436/86
[58] Field of Search .......... 364/498, 497, 496; 435/4, 5, 69.1, 69.7, 69.8; 436/15, 43, 86, 89

[56] References Cited

U.S. PATENT DOCUMENTS

| | | | |
|---|---|---|---|
| 4,704,692 | 11/1987 | Ladner | 364/496 |
| 4,717,653 | 1/1988 | Webster, Jr. | 435/5 |
| 4,853,871 | 8/1989 | Pantoliano et al. | 364/496 |
| 4,881,175 | 11/1989 | Ladner | 364/496 |
| 4,908,773 | 3/1990 | Pantoliano et al. | 364/496 |
| 4,939,666 | 7/1990 | Hardman | 364/496 |
| 4,946,778 | 8/1990 | Ladner et al. | 435/69.6 |
| 4,976,958 | 12/1990 | Shinnick et al. | 424/92 |
| 5,087,558 | 2/1992 | Webster, Jr. | 435/5 |

Primary Examiner—Vincent N. Trans
Attorney, Agent, or Firm—Spensley Horn Jubas & Lubitz

[57] ABSTRACT

A computer-assisted method for identifying protein sequences that fold into a known three-dimensional structure. The inventive method attacks the inverse protein folding problem by finding target sequences that are most compatible with profiles representing the structural environments of the residues in known three-dimensional protein structures. The method starts with a known three-dimensional protein structure and determines three key features of each residue's environment within the structure: (1) the total area of the residue's side-chain that is buried by other protein atoms, inaccessible to solvent; (2) the fraction of the side-chain area that is covered by polar atoms (O, N) or water, and (3) the local secondary structure. Based on these parameters, each residue position is categorized into an environment class. In this manner, a three-dimensional protein structure is converted into a one-dimensional environment string, which represents the environment class of each residue in the folded protein structure. A 3D structure profile table is then created containing score values that represent the frequency of finding any of the 20 common amino acids structures at each position of the environment string. These frequencies are determined from a database of known protein structures and aligned sequences. The method determines the most favorable alignment of a target protein sequence to the residue positions defined by the environment string, and determines a "best fit" alignment score, $S_{ij}$, for the target sequence. Each target sequence may then be further characterized by a ZScore, which is the number of standard deviations that $S_{ij}$ for the target sequence is above the mean alignment score for other target sequences of similar length.

26 Claims, 9 Drawing Sheets

| POSITION IN FOLD | ENVIRONMENT CLASS | AMINO ACID TYPE | | | | | | | | | | | | | | GAP PENALTY | |
|---|---|---|---|---|---|---|---|---|---|---|---|---|---|---|---|---|---|
| | | A | C | D | E | F | G | ... | R | S | T | V | W | Y | ... | Opn | Ext |
| 1 | X | 12 | −46 | 22 | 3 | −190 | 113 | ... | −32 | 32 | 12 | −91 | −214 | −94 | ... | 2 | 0.02 |
| 2 | B⁺ | −66 | −5 | −128 | −135 | 105 | −166 | ... | −80 | −117 | −76 | 60 | 102 | 112 | ... | −2 | 0.02 |
| 3 | Xα | 46 | −44 | 44 | 59 | −220 | 68 | ... | −34 | 15 | −17 | −110 | −135 | −210 | ... | 200 | 200 |
| 4 | P⁺α | 6 | −93 | 28 | 56 | −143 | −50 | ... | 50 | −18 | −5 | −48 | −114 | −79 | ... | 200 | 200 |
| 5 | Xα | 46 | −44 | 44 | 59 | −220 | 68 | ... | −34 | 15 | −17 | −110 | −135 | −210 | ... | 200 | 200 |
| 6 | P⁺α | 6 | −93 | 28 | 56 | −143 | −50 | ... | 50 | −18 | −5 | −48 | −114 | −79 | ... | 200 | 200 |
| 7 | B⁺α | −69 | −10 | −162 | −71 | 90 | −149 | ... | 6 | −147 | −150 | 68 | 50 | 85 | ... | 200 | 200 |
| 8 | Xα | 46 | −44 | 44 | 59 | −220 | 68 | ... | −34 | 15 | −17 | −110 | −135 | −210 | ... | 200 | 200 |
| 9 | P⁺α | 6 | −93 | 28 | 56 | −143 | −50 | ... | 50 | −18 | −5 | −48 | −114 | −79 | ... | 200 | 200 |
| 10 | Bα | −66 | −73 | −197 | −174 | 132 | −253 | ... | −167 | −273 | −129 | 66 | 100 | 18 | ... | 200 | 200 |
| ... | ... | ... | ... | ... | ... | ... | ... | | ... | ... | ... | ... | ... | ... | | ... | ... |

FIG. 3

Table I

| ENVIRONMENT CLASS | W | F | Y | L | I | V | M | A | G | P | C | T | S | Q | N | E | D | H | K | R |
|---|---|---|---|---|---|---|---|---|---|---|---|---|---|---|---|---|---|---|---|---|
| Bα | 1.00 | 1.32 | 0.18 | 1.27 | 1.17 | 0.66 | 1.26 | -0.66 | -2.53 | -1.16 | -0.73 | -1.29 | -2.73 | -1.08 | -1.93 | -1.74 | -1.97 | -0.34 | -1.82 | -1.67 |
| Bβ | 1.17 | 0.85 | 0.07 | 1.13 | 1.47 | 1.09 | 0.55 | -0.79 | -2.02 | -0.94 | -0.22 | -1.12 | -2.91 | -1.67 | -1.42 | -1.93 | -2.56 | -1.91 | -2.69 | -1.16 |
| B | 1.05 | 1.45 | 0.17 | 1.10 | 1.11 | 1.02 | 0.98 | -0.91 | -1.92 | 0.26 | -1.22 | -1.53 | -2.81 | -1.17 | -2.42 | -2.52 | -1.76 | -1.12 | -2.59 | -2.16 |
| B+α | 0.50 | 0.90 | 0.85 | 1.01 | 0.63 | 0.68 | 1.12 | -0.69 | -1.49 | -2.21 | -0.10 | -1.50 | -1.47 | -0.23 | -0.61 | -0.71 | -1.62 | 0.23 | -0.78 | -0.06 |
| B+β | 0.01 | 1.18 | 1.06 | 0.76 | 1.31 | 1.06 | 0.64 | -1.55 | -2.26 | -0.49 | -0.87 | -2.27 | -1.77 | -1.22 | -2.07 | -1.07 | -1.41 | -0.77 | -1.14 | -0.20 |
| B+ | 1.02 | 1.05 | 1.12 | 0.84 | 0.81 | 0.60 | 0.90 | -0.66 | -1.66 | 0.19 | -0.05 | -0.76 | -1.17 | -0.76 | -0.66 | -1.35 | -1.28 | 0.46 | -2.34 | -0.80 |
| B++α | 0.92 | -0.03 | 0.58 | 0.15 | 0.04 | -0.02 | 0.89 | -0.57 | -1.86 | -0.68 | -1.56 | -0.57 | -0.96 | 0.22 | -0.06 | 0.08 | -0.50 | 0.73 | 0.43 | 0.96 |
| B++β | 0.75 | 0.81 | 0.17 | 0.18 | 0.54 | 0.56 | -0.57 | -0.93 | -1.93 | -0.34 | -0.54 | -0.44 | -0.74 | 0.21 | -0.24 | -0.14 | -0.86 | 0.82 | -0.53 | 0.13 |
| B++ | 1.07 | 0.70 | 1.13 | 0.35 | -0.17 | -0.03 | 0.23 | -0.96 | -0.98 | -0.13 | -1.20 | -0.53 | -0.54 | 0.05 | 0.04 | -0.36 | -1.05 | 1.01 | 0.10 | 0.66 |
| Pα | -1.35 | -0.82 | -0.59 | -0.52 | -0.24 | 0.10 | -0.03 | 0.73 | -0.49 | -0.25 | 0.95 | 0.31 | 0.34 | -0.14 | -0.54 | -0.17 | -0.25 | -0.52 | -0.21 | -0.28 |
| Pβ | 0.36 | -0.49 | 0.17 | -1.03 | 0.20 | 0.46 | -0.27 | 0.64 | -0.82 | -0.55 | 1.49 | 0.93 | 0.33 | -2.27 | -1.32 | -0.73 | -1.07 | -0.42 | -1.21 | -0.77 |
| P | -1.26 | -1.20 | -1.31 | -0.62 | -0.23 | -0.01 | -1.19 | -0.46 | -0.24 | 0.66 | 1.35 | 0.56 | 0.49 | -0.63 | -0.13 | -0.61 | 0.38 | -1.12 | -0.74 | -1.29 |
| P+α | -1.14 | -1.43 | -0.79 | -0.35 | -0.54 | -0.48 | -0.45 | 0.06 | -0.50 | -0.26 | -0.93 | -0.05 | -0.18 | 0.55 | -0.05 | 0.56 | 0.28 | 0.06 | 0.61 | 0.50 |
| P+β | -0.79 | -0.54 | -0.84 | -1.30 | -0.33 | 0.13 | -0.72 | -0.55 | -0.98 | -1.29 | -0.57 | 0.84 | 0.59 | -0.08 | -0.16 | 0.32 | 0.19 | -0.87 | 0.59 | 0.10 |
| P+ | -0.82 | -0.86 | -0.51 | -0.70 | -1.09 | -0.88 | -0.89 | -0.15 | -0.40 | 0.44 | -0.60 | 0.06 | 0.26 | 0.27 | 0.50 | 0.27 | 0.49 | 0.13 | 0.44 | 0.30 |
| Xα | -1.35 | -2.20 | -2.10 | -1.58 | -2.76 | -1.10 | -0.72 | 0.46 | 0.68 | 0.04 | -0.44 | -0.17 | 0.15 | 0.36 | 0.28 | 0.59 | 0.44 | 0.19 | 0.13 | 0.34 |
| Xβ | 0.64 | -0.90 | 0.30 | -1.66 | -1.47 | -1.74 | -0.68 | 0.06 | 1.46 | -0.96 | -0.24 | 0.14 | 0.65 | -0.19 | -0.06 | -0.16 | -0.78 | -0.83 | -0.52 | -0.49 |
| X | -2.14 | -1.90 | -0.94 | -1.19 | -1.61 | -0.91 | -1.67 | 0.12 | 1.13 | 0.20 | -0.46 | 0.12 | 0.32 | -0.03 | 0.41 | -0.03 | 0.22 | -0.25 | -0.14 | -0.32 |

FIG. 6

Table II

| Protein | ZScore(3D) | ZScore(1D) | Percent Identity |
|---|---|---|---|
| cAMP receptor protein-*E. coli* | 46.53 | 72.99 | 100.0 |
| cAMP receptor protein-*S. typhimurium* | 44.13 | 72.45 | 99.5 |
| Hypothetical 24.1K protein-*L. casei* | 11.84 | 12.74 | 25.6 |
| Regulatory protein fixK-*Rhizobium meliloti* | 10.65 | 9.26 | 21.1 |
| Regulatory protein FNR-*E. coli* | 9.20 | 7.03 | 21.2 |
| Protein kinase,cGMP-dependent-Bovine | 8.24 | — | 22.0 |
| Protein kinase type III regulatory chain - Fruit fly | 6.62 | — | 20.9 |
| DNA polymerase accessory protein 44-Bacteriophage T4 | 6.58 | — | 19.7 |
| Protein kinase type II regulatory chain-Fruit fly | 6.47 | — | 20.9 |
| Protein kinase, cAMP-dependent, regulatory chain II-alpha-Human | 6.33 | — | 21.2 |
| Protein kinase type I regulatory chain-Fruit fly | 6.15 | — | 20.9 |
| Protein kinase, cAMP-dependent, type II regulatory chain-Bovine | 6.06 | — | 20.9 |

FIG. 7

METHOD TO IDENTIFY PROTEIN SEQUENCES THAT FOLD INTO A KNOWN THREE-DIMENSIONAL STRUCTURE

This is a continuation of application Ser. No. 07/728,640 filed on Jul. 11, 1991, now abandoned.

BACKGROUND OF THE INVENTION

1. Field of the Invention

This invention relates to a computer-assisted method for identifying protein sequences that fold into a known three-dimensional structure.

2. Related Art

Proteins (or polypeptides) are linear polymers of amino acids. The polymerization reaction which produces a protein results in the loss of one molecule of water from each amino acid, and hence proteins are often said to be composed of amino acid "residues." Natural protein molecules may contain as many as 20 different types of amino acid residues, each of which contains a distinctive side chain. The particular linear sequence of amino acid residues in a protein defines the primary sequence, or primary structure, of the protein. The primary structure of a protein can be determined with relative ease using known methods.

Proteins fold into a three-dimensional structure. The folding is determined by the sequence of amino acids and by the protein's environment. Examination of the three-dimensional structure of numerous natural proteins has revealed a number of recurring patterns. Patterns known as alpha helices, parallel beta sheets, and anti-parallel beta sheets are the most common observed. A description of such protein patterns is provided by Dickerson, R. E., et al. in *The Structure and Action of Proteins*, W. A. Benjamin, Inc. California (1969). The assignment of each amino acid residue to one of these patterns defines the secondary structure of the protein.

The helices, sheets, and turns of a protein's secondary structure pack together to produce the folded three-dimensional, or tertiary, structure of the protein.

In the past, the three-dimensional structure of proteins has been determined in a number of ways. Perhaps the best known way of determining protein structure involves the use of the technique of x-ray crystallography. A general review of this technique can be found in *Physical Bio-chemistry*, Van Holde, K. E. (Prentice-Hall, New Jersey 1971), pp. 221–239, or in Physical Chemistry with Applications to the Life Sciences, D. Eisenberg & D. C. Crothers (Benjamin Cummings, Menlo Partk 1979). Using this technique, it is possible to elucidate three-dimensional structure with good precision. Additionally, protein structure may be determined through the use of the techniques of neutron diffraction, or by nuclear magnetic resonance (NMR). See, e.g., *Physical Chemistry*, 4th Ed. Moore, W. J. (Prentice-Hall, New Jersey 1972) and *NMR of Proteins and Nucleic Acids*, K. Wüthrich (Wiley-Interscience, New York 1986).

The three-dimensional structure of many proteins may be characterized as having internal surfaces (directed away from the aqueous environment in which the protein is normally found) and external surfaces (which are exposed to the aqueous environment). Through the study of many natural proteins, researchers have discovered that hydrophobic residues (such as tryptophan, phenylalanine, tyrosine, leucine, isoleucine, valine, or methionine) are most frequently found on the internal surface of protein molecules. In contrast, hydrophilic residues (such as aspartate, asparagine, glutamate, glutamine, lysine, arginine, histidine, serine, threonine, glycine, and proline) are most frequently found on the external protein surfaces. The amino acids alanine, glycine, serine, and threonine are encountered with more nearly equal frequency on both the internal and external protein surfaces.

The biological properties of proteins depend directly on the proteins three-dimensional (3D) conformation. The 3D conformation determines the activity of enzymes, the capacity and specificity of binding proteins, and the structural attributes of receptor molecules. Because the three-dimensional structure of a protein molecule is so significant, it has long been recognized that a means for readily determining a protein's three-dimensional structure from its known amino acid sequence would be highly desirable. However, it has proved extremely difficult to make such a determination. One difficulty is that each protein has an astronomical number of possible conformations (about $10^{16}$ for a small protein of 100 residues; see K. A. Dill, *Biochemistry*, 24, 1501–1509, 1985), and there is no reliable method for picking the one conformation stable in aqueous solution. A second difficulty is that there are no accurate and reliable force laws for the interaction of one part of a protein with another part, and with water. Proteins exist in a dynamic equilibrium between a folded, ordered state and an unfolded, disordered state. These and other factors have contributed to the enormous complexity of determining the most probable relative 3D location of each residue in a known protein sequence.

The protein folding problem, the problem of determining a proteins three-dimensional tertiary structure from its amino acid sequence, or primary structure, has defied solution for over 30 years. In the last decade, however, the increase in the number of known protein sequences, and the fact that many sequences have been found to fold into the same basic three-dimensional structure, have focused attention on a related problem: the inverse protein folding problem. The inverse protein folding problem asks, given a known three dimensional protein structure, which amino acid sequences fold into that structure?

As a result of the molecular biology revolution, the number of known protein sequences is about 50 times greater than the number of known three-dimensional protein structures. This disparity hinders progress in many areas of biochemistry because a protein sequence has little meaning outside the context of the three-dimensional structure. The disparity is less severe than the numbers might suggest, however, because different proteins often adopt similar three-dimensional folds. As a result, each new protein structure can serve as a model for other protein structures. These structural similarities occur because the current array of protein structures probably evolved from a small number of primordial folds. If the number of folds is indeed limited, it is possible that x-ray crystallographers and NMR spectroscopists may eventually describe examples of essentially every fold. In that event, protein structure prediction theoretically would reduce, at least in crude form, to the inverse protein folding problem—the problem of identifying which fold in this limited repertoire a particular amino acid sequence adopts.

The inverse protein folding problem is most often approached by seeking sequences that are similar to the sequence of a protein whose structure is known. If a sequence relationship can be found, it can often be inferred that the protein of known sequence but unknown structure adopts a fold similar to the protein of known structure. The strategy works well for closely related sequences, but structural similarities can go undetected as the level of sequence identity drops below about 25 percent.

A more direct attack on the inverse protein folding problem has been to search for sequences that are compatible with a given structure. In this "tertiary template" method, the backbone of a known protein structure—the amino acid residues less the side chains—is kept fixed and the side-chains in the protein core were then replaced and tested combinatorially by computer, to find which combination of new side-chains could fit into the core. A set of core sequences is thereby enumerated that could in principle be tolerated in the protein structure. In this manner, the method of tertiary templates provides a direct link between possible three-dimensional structure and known sequence. See J. W. Ponder, F. M. Richards, *J. Mol. Biol.*, 93, 775–791 (1987).

The rules used to relate one-dimensional amino acid sequences to possible three-dimensional structures in the tertiary template method may be excessively rigid. Proteins that fold into similar structures can have large differences in the size and shape of residues at equivalent positions. These changes are tolerated not only because of replacements or movements in nearby sidechains, but also as a result of shifts in the protein backbone. Moreover, insertions and deletions in the amino acid sequence, which are commonly found in related protein structures, are not considered in the implementation of tertiary templates. To describe realistically the sequence requirements of a particular fold, the constraints of a rigid backbone and a fixed spacing between core residues must somehow be relaxed.

Another approach, suggested by work done by one of the present inventors, is a profile method that characterizes the amino acid sequences of families of proteins aligned by sequence or structural similarities. The profile method builds a table of weighted values that reflect the frequency that amino acid residues are likely to be located at a particular position in the sequence of amino acids forming the proteins. The profile table thus characterizes the entire family of proteins upon which the table is based. A target amino acid sequence is compared to the profile, using a known dynamic programming method, to determine a final "best fit" score. Insertions and deletions of amino acids in the target sequence are provided for by appropriate "gap opening" and "gap extension" penalties that affect the final score. See M. Gribskov, A. D. McLachlan, and D. Eisenberg, *Proc. Natl. Acad. Sci. U.S.A.*, 84, 4355 (1987); M. Gribskov, M. Homyak, J. Edenfield, and D. Eisenberg, CABIOS 4, (1988); M. Gribskov and D. Eisenberg, in *"Techniques in Protein Chemistry"* (T. E. Hugli, ed.), p. 108. Academic Press, San Diego, Calif., 1989; M. Gribskov, R. Lüthy, and D. Eisenberg, *Meth. in Enz.* 183, 146 (1990).

The profile method is useful for learning whether a target protein sequence belongs to a known family of sequences, and some inferences can be made that the target sequence has a three-dimensional structure similar to the structures of the known family of sequences. However, the profile method does not directly take into account specific structural characteristics of the known family of sequences, since the profile table is constructed based only upon alignments of amino acid sequences within selected proteins of known structure. Thus, a large amount of information inherent in a known structure is simply ignored in a sequence profile.

Thus, it would be desirable to develop a method for relating a one-dimensional target sequence directly to a known 3D structure which effectively utilizes the information about the accommodation of sequence changes that is inherent in a known 3D structure.

The present invention provides such a method, using a novel method of profiling structural characteristics of families of proteins with known three-dimensional structures, and a computer-assisted search procedure for comparing target amino acid sequences to such profiles.

SUMMARY OF INVENTION

The present invention establishes a link between known three-dimensional structures and target amino acid sequences in a way that simulates the malleability of real proteins. The inventive method attacks the inverse protein folding problem by finding target sequences that are most compatible with profiles representing the structural environments of the residues in known three-dimensional protein structures.

The method starts with a known three-dimensional protein structure and determines three key features of each residue's environment within the structure: (1) the total area of the residue's side-chain that is buried by other protein atoms, inaccessible to solvent; (2) the fraction of the side-chain area that is covered by polar atoms (O, N) or water, and (3) the local secondary structure. Based on these parameters, each residue position is categorized into an "environment class". In this manner, a three-dimensional protein structure is converted into a one-dimensional "environment string", or characterizing sequence, which represents the environment class of each residue in the folded protein structure. A 3D structure profile table is created containing score values that represent the frequency of finding any of the 20 common amino acids structures at each position of the environment string. These frequencies are determined from a database of known protein structures and aligned sequences. The method determines the most favorable alignment of a target protein sequence to the residue positions defined by the environment string, and determines a "best fit" alignment score, $S_{ij}$, for the target sequence. Each target sequence may then be further characterized by a ZScore, which is the number of standard deviations that $S_{ij}$ for the target sequence is above tile mean alignment score for other target sequences of similar length.

Examples of the method are presented for four families of proteins—the globins, cyclic AMP receptor-like proteins, the periplasmic binding proteins, and the actins. The method indicates that several repressors have a folding domain that is similar to that of the periplasmic binding proteins. Moreover, the method is able to detect the structural similarity of the actins and 70K heat shock proteins, even though these proteins share no detectable sequence similarity. These examples suggest that the inventive method will permit assignment of many amino acid sequences to known three-dimensional structures.

The details of the preferred embodiment of the present invention are set forth in the accompanying drawings and the description below. Once the details of the invention are known, numerous additional innovations and changes will become obvious to one skilled in the art.

DESCRIPTION OF THE DRAWINGS

FIG. 3 is part of the 3D structure profile table for sperm whale myoglobin, in accordance with the present invention.

FIG. 6 is Table I, representing environment classes for matching 20 common amino acids.

FIG. 7 is Table II, representing proteins with Zscores greater than 6.0, derived from a sequence homology search using a sequence profile constructed from the cyclic AMP receptor protein (CRP) sequence with a 3D compatibility search using a 3D structure profile of the CRP structure.

Like reference numbers and designations in the drawings refer to like elements.

DETAILED DESCRIPTION OF THE INVENTION

Throughout this description, the preferred embodiment and examples shown should be considered as exemplars, rather than limitations on the present invention.

Figure 1:
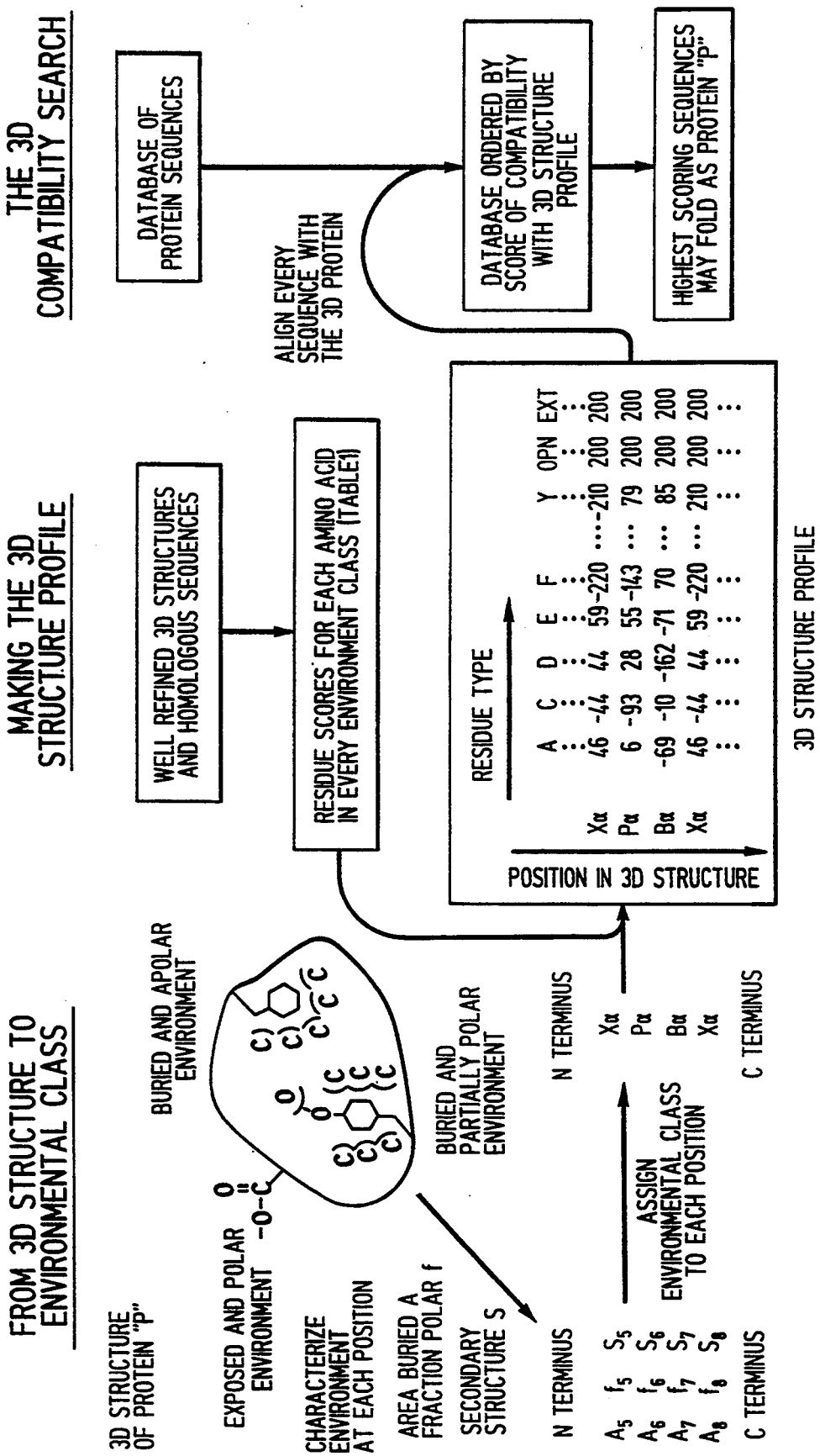
FIG. 1 is a diagram of the preferred method for determining an environment string, defining a 3D structure profile table, and performing a 3D compatibility search in accordance with the present invention.

An overview of the inventive method is diagrammatically shown in FIG. 1. The method starts with a known three-dimensional protein structure P and determines three key features of each residue's environment within the structure:

(1) the total area A of the residue's side-chain that is buried by other protein atoms, inaccessible to solvent;

(2) the fraction f of the side-chain area that is covered by polar atoms (O, N) or water; and (3) the local secondary structure s.

Based on these parameters, each residue position is categorized into an "environment class". In this manner, a three-dimensional protein structure P is converted into a one-dimensional "environment string", or characterizing sequence, E which represents the environment class of each residue in the folded protein structure. A 3D structure profile table T is then created containing score values that represent the frequency of finding any of the 20 common amino acids structures at each position of the environment string E. These frequencies are determined from a database of known protein structures and aligned sequences. Thereafter, using known search techniques, the method determines the most favorable alignment of a target protein sequence S to the residue positions defined by the environment string E, and determines a "best fit" score $S_{ij}$ for the target sequence S with respect to the 3D structure profile table T. Each target sequence may then be further characterized by a ZScore, which is the number of standard deviations that $S_{ij}$ for the target sequence is above the mean alignment score for other target sequences of similar length.

The alignment of an environment string with a protein sequence relies on the clear preferences of each of the twenty amino acids for different environmental classes. For example, it is rare to find a charged residue buried in a non-polar environment. Thus, by determining the environment class of a given position in a protein structure, it is possible to assign a score for finding each of the 20 amino acid types at that position in some related protein structure. These scores are defined as "3D-1D scores". The 3D-1D scores can then be used in a sequence alignment algorithm to find the best alignment of a target amino acid sequence to a particular environment string. The quality of alignment is taken as a measure of the compatibility of the target sequence with the three-dimensional structure upon which the environment string was based.

The inventive method simulates the malleability of protein structures because no rigid tests for compatibility are applied. In particular, gaps are allowed in the alignment of a target sequence to an environment string, and unfavorable amino acids can be placed at any position, provided these low scores are overcome by enough favorable amino acid-environment pairings (high 3D-1D scores). Because the quality of the alignment to an environment string is not related to sequence similarity in any simple way, the sequence database searches using the environment strings are termed "3D compatibility searches" to distinguish them from homology searches.

Generation of an Environment String

The first step in the inventive method is to determine an environmental string for a protein having a known 3D structure. This is done as follows in the preferred embodiment:

each residue in the known three-dimensional protein structure is characterized in terms of A, f, and s values;

(2) each position corresponding to a residue is assigned to one of 18 environment classes, based upon the A, f, and s values for the residue.

Figure 2:
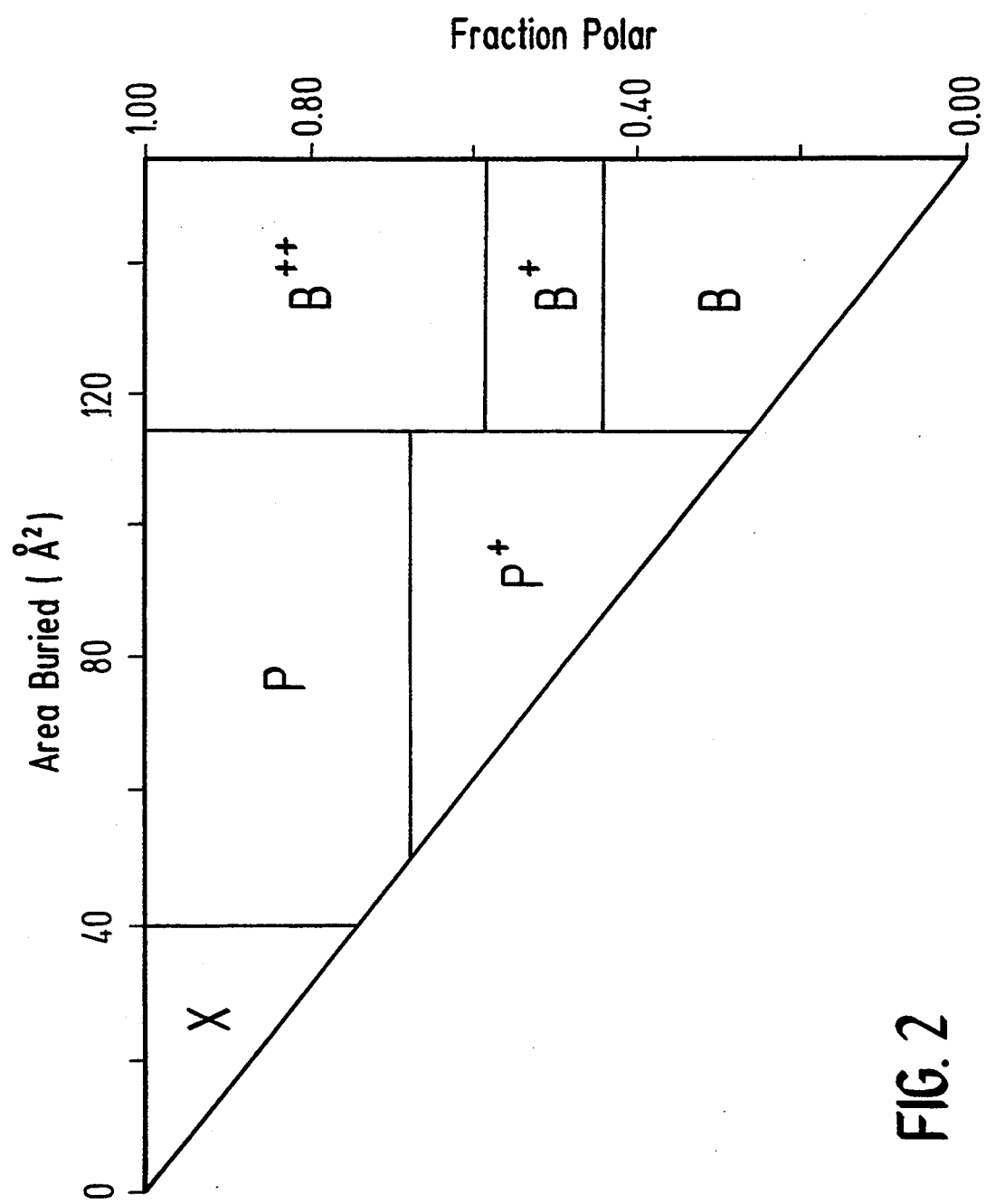
FIG. 2 is a diagram showing six of the preferred side-chain environmental classes used to determine an environment string in accordance with the present invention.

Six of the environment classes represent side-chain environments determined by A, the total area buried in the protein structure and f, the fraction of the side-chain area covered by polar atoms. Referring to FIG. 2, the environment of a side-chain is first classed as buried, partially buried, or exposed, according to the solvent-accessible surface area of the side-chain. The buried and partially buried residue environments are further subdivided based on the fraction of the environment consisting of polar atoms. The buried class is divided into three subclasses, labeled B, B+, and B++, in order of increasing environmental polarity. Similarly, the residue positions in the partially buried class are divided into two subclasses, labeled P and P+, in order of increasing polarity. Water is treated as polar, so exposed positions are necessarily in a polar environment. Consequently, the exposed side-chain category, labeled X, is not subdivided into polarity classes.

For example, for a particular residue using the preferred embodiment, if $A > 114 \text{ Å}^2$, the residue, is placed in environment class B if $f < 0.45$; in environment class $B^+$ if $0.45 \leq f < 0.58$; and in environment class $B^{++}$ if $f \geq 0.58$. If $40 < A \leq 114 \text{ Å}^2$, the residue is placed in environment category P if $f < 0.67$ and in environment class $P^+$ if $f \geq 0.67$. A residue is placed in the exposed environment category X if less than 40 Å$^2$ of the side-chain is buried. (The determination of the preferred cutoff values is explained below in connection with TABLE I).

To account for the slight preferences of certain residue types to be in particular secondary structures, residues in the side-chain environment classes are further distributed into three secondary structure types: $\alpha$ helix, $\beta$ sheet and Other. This gives a total of 18 environment classes into which a particular residue may be categorized in the preferred embodiment (i.e., six side-chain environments times three secondary structure types).

Although only three subclasses are shown for the buried class, and only two subclasses are shown for the partially buried class, other numbers of subclasses could be used to more finely grade variations between residue environments. Similarly, the definition of "partially buried" may be divided further to account for finer distinctions in residue environments. In the same manner, additional secondary structure types may be explicitly considered in defining environment classes.

Furthermore, other structural properties of a residue can be used to characterize its environment and define environmental classes, such as conformational angles $\phi$ and $\psi$, apolar (i.e., carbon and sulfur) area buried, polar (i.e., oxygen and nitrogen) area buried, depth of burial relative to the protein surface, and/or side-chain volume. In general, the inventive method encompasses characterizing each residue of a known protein structure by n structural properties $P_1, P_2, \ldots P_n$ at each position of the folded 3D protein structure.

In the preferred embodiment, to determine A and f for each side-chain, the solvent-accessible surface area of each atom is determined by first centering a sphere at the nucleus of each protein atom (other than hydrogen). The sphere has a radius equal to the sum of the van der Waals radius and the radius of a water molecule. Each sphere was sampled at points placed about every 0.75 Å along its surface. If a point was not within the sphere of any other atom, it is deemed accessible to water, otherwise it is treated as buried. The fraction of points accessible to water is then proportional to the solvent-accessible surface area. The total area A of a side-chain buried in the protein structure is then determined by subtracting the free solvent accessibility of the side-chain (defined as the solvent-accessible area of side-chain X in a Gly-X-Gly tripeptide), and the total solvent-accessible area of the side-chain in the protein. C$\alpha$ atoms were treated as part of the side-chain. Van der Waals radii were from T. J. Richmond, F. M. Richards, *J. Mol Biol.*, 119, 537 (1978), and free side-chain areas were from D. A. Eisenberg, M. Wesson, M. Yamashita, *Chemica Scripta*, 29A, 217–221 (1989). The fraction f of the side-chain covered by polar atoms is the number of sample points that are exposed to solvent or buried by polar atoms, divided by the total number of sample points. If a point is buried by both polar atoms and non-polar atoms, the closer type of atom takes precedence. Points covered by atoms of the side-chain under consideration were not counted in the determination of f.

Generation of 3D Structure Profiles

To search a sequence database for the amino acid sequences most compatible with a particular environment string, the inventive method uses a variation of the profile method discussed above. While the profile method was originally developed for detecting sequence homology, it has been expanded to accommodate the purposes of the present invention. Using some of the concepts of the profile method, a 3D structure profile is generated for each environment string.

A 3D structure profile is a position-dependent scoring table in which each position of an environment string is assigned 20 scores ("3D-1D scores"), representing the likelihood of finding any of the 20 amino acids at that position. In previous implementations of the profile method, these scores were based on sequence information from families of sequences. What distinguishes the present 3D structure profiles from sequence profiles is that now the profile scores are values based upon the structural environments of residues in a known three-dimensional structure, rather than simple sequence information.

A 3D structure profile table thus establishes a connection between a known three-dimensional protein structure, represented by a one-dimensional environmental string, and a one-dimensional target sequence, by specifying a 3D-1D score for each residue type in each environmental class.

The 3D-1D scores for matching the 20 common amino acids with the 18 defined environment classes used in the preferred embodiment are given in TABLE I. The score for pairing a residue i with an environment j is given by the information value, $$3D\text{-}1D \text{ Score } ij = \ln\left(\frac{P(i:j)}{P_i}\right)$$

where P(ij) is the probability of finding residue i in environment j, and Pi is the overall probability of finding residue i in any environment. In developing the preferred embodiment of the present invention, these probabilities were determined statistically from a database of 16 known protein structures and sets of homologous sequences aligned to a sequence of known structure. The database used is described in R. Lüthy, A. McLachlan, D. Eisenberg, *Proteins: Structure, Function and Genetics*, 10, 224–239 (1991) (hereby incorporated by reference).

More specifically, for each residue position in each of the aligned set of 16 known protein sequences, the A, f, and s values for the residue were determined from the known 3D structure. Thereafter, the environment class for the residue position was determined, and the number of each residue type found at the position within the set of aligned sequences was counted. A residue type was counted only once per position. For example, if there were 10 aspartates and 1 glycine found at a position in a set of aligned sequences, then the aspartate and glycine counts were both incremented only by one. The total number of residue replacements in the database used was 8273. If the number of residues i in an environment j was found to be zero, the number was increased to 1 so that P(ij) was never zero.

Cutoffs for the environment categories shown in FIG. 2 were adjusted iteratively to maximize the total 3D-1D score summed over all residues in the database:

$$\text{Total 3D-1D Score} = \sum_{ij} N_{ij} \ln\left(\frac{P(i,j)}{P_i}\right)$$

where $N_{ij}$ is the number of residues i in environment j. In this case, if $N_{ij}$ was zero, the number was not increased to 1. Instead, that term in the sum was treated as zero.

In general, residues with large hydrophobic sidechains are found in the buried classes B, B+, and B++, while hydrophilic residues are favored in the exposed class X. If, however, a buried position has a polar environment (an environment with potential hydrogen bond donors and acceptors), it should be less unfavorable to place polar side-chains at that position. This trend is evident among the polar residues.

For example, glutamine has unfavorable 3D-1D scores in the most non-polar, buried environment B, but is favorable in the polar, buried environment B++. Within each environmental class, the preference for the secondary structure types generally follow the trends found in earlier studies. For example, lysine has a higher propensity to be in a helix than in a sheet. See P. Y. Chou, G. D. Fasman, *Adv. Enz.*, 47, 45–148 (1978). A similar trend is seen in TABLE I. In short, the 3D-1D scores of TABLE I provide the link of 3D protein structure to 1D environment string sequence in the 3D structure profile method in the same way that the Dayhoff mutational matrix supplies the link between two sequences in the earlier sequence profile method. See M. Gribskov, A. D. McLachlan, and D. Eisenberg, *Proc. Natl. Acad. Sci. U.S.A.*, 84, 4355 (1987)

Part of the 3D structure profile table for sperm whale myoglobin is shown in FIG. 3. Each row in the 3D structure profile represents an amino acid residue position in the known three-dimensional structure. The second column gives the environment class of each residue position in the folded protein (i.e., the second column is the environment string for sperm whale myoglobin), determined as described above. The following 20 columns for each residue position give the 3D-1D score for placing each of the 20 common amino acids in the environment found at that position in the structure.

The last two columns of FIG. 3 give penalty values for opening a gap (Opn) and for extending the length of the gap at a position (Ext). In the preferred embodiment, Opn is set to be approximately three times the largest 3D-1D score in a row, and Ext is set to be 1% of Opn. The default value for Opn is 5, and for Ext is 0.05. However, the values for Opn and Ext may be set based upon any desired criteria. For example, since gaps are known to occur most frequently between regions of secondary structure, it can be advantageous to lower the penalty values in non-secondary structure regions. In FIG. 3, the first two positions are not in a secondary structure, and are given low penalty values.

In addition, a user may specify weights, or multipliers, m to apply to the Opn and/or Ext values. Lower m values result in lesser penalties for opening or extending a gap. In the preferred embodiment, the values for these multipliers m are 100 for every row of the profile, but are user adjustable. The penalty multipliers may be different for the Opn and the Ext values. In addition, the penalty value and penalty multipliers may be generated in other ways; one way is discussed in M. Gribskov, R. Lüthy, and D. Eisenberg, *Meth. in Enz.* 183, 146 (1990).

The example shows the first 10 positions of the sperm whale myoglobin 3D structure profile. The actual profile is 153 positions long, the length of the sperm whale myoglobin sequence. The scores placed in each row are from the corresponding 3D-1D scores of TABLE I, multiplied by 100. The most effective gap penalties were determined empirically. In this case, the gaps in helical regions were forbidden by setting very high gap penalties for the helical positions (positions 3 through 10 in the profile). In contrast, relatively low gap opening (Opn) and gap extension (Ext) penalties were used for the coil regions (positions 1 and 2).

In an alternative embodiment, the features of a residue's environment can be used to directly calculate the 3D-1D score for the residues position in the 3D structure, without the need to assign the residue to a discrete environmental class. Each 3D-1D score is a frequency value derived from known protein sequences having known three-dimensional structures, each value being generated as the frequency of occurrence of the n structural properties $P_1, P_2, \ldots P_n$ for each amino acid residue of the known protein sequences.

In particular, a 3D-1D score S(a) can be determined for each amino acid residue type a in a three-dimensional structure in terms of the values for n structural properties $P_1, P_2, \ldots P_n$ in accordance with the following equation:

$$S(a) = c_1(a)P_1 + c_2(a)P_2 + \ldots c_n(a)P_n$$

where $c_1(a), c_2(a), \ldots c_n(a)$ are empirically determined constants. The constants $c_1(a), c_2(a), \ldots c_n(a)$ are preferrably determined by a least squares fitting procedure applied to 20 equations $S(a)_i$, one for each type a of the common amino acids. The calculated profile score S(a) is fitted to the "observed" score of a sequence (not 3D structure) profile by varying the constants $c_1(a), c_2(a), \ldots c_n(a)$. However, other numerical or analytical fitting procedure may be used to determine $c_1(a), c_2(a), \ldots c_n(a)$.

3D Compatibility Searching

Once a 3D structure profile table is generated for a protein sequence having a known 3D structure, a comparison may be made between the table and amino acid sequences having unknown structures. The inventive method determines the most favorable alignment of a target protein sequence S to the residue positions defined by the environment string E, and determines a "best fit" score $S_{ij}$. Each target sequence may then be further characterized by a ZScore, which is the number of standard deviations that $S_{ij}$ for the target sequence is above the mean alignment score for other target sequences of similar length. The quality of alignment is taken as a measure of the compatibility of the target sequence with the three-dimensional structure upon which the environment string was based.

In particular, all sequences in a database of target sequences are aligned with the 3D structure profile using a dynamic programming algorithm, which allows insertions and deletions in the alignment. Preferred dynamic programming algorithms are taught in S. B. Needleman, C. D. Wunsch, *J. Mol. Biol.*, 48, 443–453 (1970) and T. F. Smith, M. S. Waterman, *Adv. Appl. Math.*, 2, 482–489 (1981), and their use is discussed and demonstrated in M. Gribskov, A. D. McLachlan, and D. Eisenberg, *Proc. Natl. Acad. Sci. U.S.A.*, 84, 4355 (1987); M. Gribskov, M. Homyak, J. Edenfield, and D. Eisenberg, *CABIOS* 4, (1988); M. Gribskov and D. Eisenberg, in "*Techniques in Protein Chemistry*" (T. E. Hugli, ed.), p. 108. Academic Press, San Diego, Calif., 1989; M. Gribskov, R. Lüthy, and D. Eisenberg, *Meth. in Enz.* 183, 146 (1990) (all incorporated herein by reference). Any comparable search technique that takes into account such insertions and deletions could also be used.

In the preferred embodiment, the dynamic programming algorithm defines the score $S_{ij}$ recursively as:

$$S_{ij} = \text{Profile}(j, \text{column}_{a_i}) + \max \begin{bmatrix} S_{i-1,j-1}, \\ \max_{2 \leq k \leq j-1}(S_{i-1,j-k} - w_k), \\ \max_{2 \leq l \leq i-1}(S_{i-1,j-1} - w_l) \end{bmatrix}$$

where $S_{ij}$ is the score for the alignment of the target sequence with the 3D structure profile such that position i of the target sequence is aligned with row j of the profile, and the penalties $w_k$ and $w_l$ are given by:

$$w_k = p_{open}(j - k) \cdot m_{open} + \sum_{j'=j-k}^{j-2} p_{extend}(j') \cdot m_{extend}$$

$$w_l = p_{open}(j - 1) \cdot m_{open} + (l - 1) \cdot p_{extend}(j - 1) \cdot m_{extend}$$

with $m_{open}$ and $m_{extend}$ being global penalty multipliers for the 3D structure profile, $p_{open}$ and $p_{extend}$ being the position-specific gap-opening (Opn) and gap-extension penalties (Ext), and j-k being the gap length. In the preferred embodiment, the user can accept default values for $m_{open}$ and $m_{extend}$, or enter other values when generating the profile.

The score $S_{ij}$ for the best alignment of the profile to each target sequence is tabulated, and the mean value and standard deviation of best alignment scores for all target sequences are computed. The match of a target sequence to a 3D structure profile representing a particular protein fold is expressed quantitatively by its ZScore. The ZScore for each target sequence is its number of standard deviations above the mean alignment score for other target sequences of similar length. Experience has shown that a vast majority of target sequences receiving ZScores above about 7 are folded in the same general way as the known three-dimensional structure represented by the 3D structure profile.

Following are four examples of 3D compatibility searches using various 3D structure profiles generated in accordance with the present invention.

1. 3D Compatibility Search Using a 3D Structure Profile for Myoglobin

Figure 4:
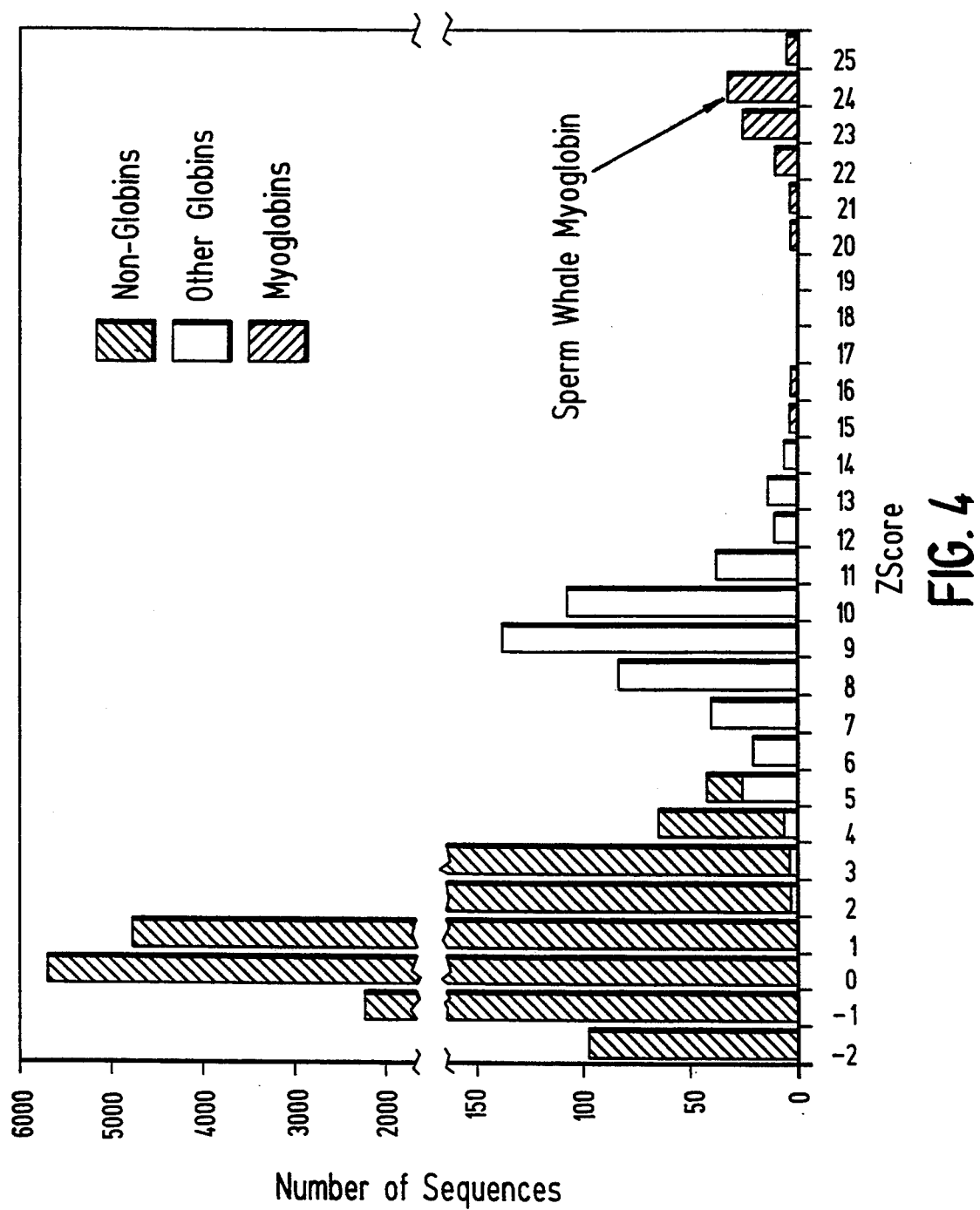
FIG. 4 is a graph showing the results of a 3D compatibility search for the structure of sperm whale myoglobin

A demonstration that a 3D structure profile can actually detect sequences compatible with a known three-dimensional structure is offered by the well-characterized globin family. FIG. 4 shows the ZScores for all sequences in the database aligned to a 3D structure profile constructed from the coordinates of sperm whale myoglobin. Myoglobin sequences are represented by black bars, other globin sequences are represented by white bars, and all other sequences are shown by gray bars. Sperm whale myoglobin is the eighth highest scoring protein (ZScore=23.7). Gaps were not allowed in helical regions (as defined in the protein data bank file). In non-helical regions, a gap opening penalty of 2.0 and a gap extension penalty of 0.02 was used.

As shown, 511 of the 544 globin sequences scored more highly than any non-globin sequence. The results shown in FIG. 4 from the 3D structure profile are qualitatively similar to the results of a prior art sequence profile (not shown) constructed from the myoglobin sequence, but differs in two significant aspects. First, as a result of the fact that no specific sequence information was used to construct the 3D structure profile, sperm whale myoglobin is not the highest scoring protein sequence in the database. In a sequence homology search, the sperm whale myoglobin sequence must be the highest scoring sequence, since it will produce a perfect match. Second, the 3D structure profile was found to be somewhat more selective for globin sequences than is the sequence profile computed from the sperm whale myoglobin sequence. In general, it was found that a 3D structure profile is less sensitive to specific sequence relationships and more sensitive to general structural similarity than a sequence profile used with a sequence homology search.

2. 3D Compatibility Search Using a 3D Structure Profile for Cyclic AMP Receptor Protein The greater sensitivity of a 3D compatibility search over a simple sequence homology search in detecting distant structural relationships is also seen in the case of the cyclic AMP receptor protein (CRP). CRP is a DNA binding protein responsible for the activation of transcription when bound to the effector molecule cAMP. Its sequence is similar to those of a number of other DNA binding proteins as well as the cAMP dependent protein kinase family.

TABLE II compares the results of (1) a sequence homology search using a sequence profile constructed from the CRP sequence with (2) a 3D compatibility search using a 3D structure profile of the CRP structure. All proteins with ZScores greater than 6.0 in either the sequence homology search or the compatibility search are, listed. "ZScore (1D)" refers to the scores obtained from a sequence homology search using a sequence profile constructed using the *E. coil* CRP sequence. "ZScore (3D)" refers to the scores obtained from a 3D compatibility search using a 3D structure profile constructed from the *E. coil* CRP structure. Percent identity refers to the percent of identical amino acids in the sequences aligned using the program BEST-FIT, described in J. Devereux, P. Haeberli, 0. Smithies, *Nucleic Acids Research*, 12, 387–395 (1984). For the sequence homology search, a gap opening penalty of 4.5 and a gap extension penalty of 0.05 was used. For the 3D structure compatibility search, a gap opening penalty of 5.0 and a gap extension penalty of 0.05 was used. In the sequence homology search, the next highest scoring protein after fnr was BamHIORF4 protein from fowlpox virus, which had an insignificant ZScore of 4.90.

Both profiles detect significant relationships between CRP and the fnr and FixK proteins, both known DNA binding proteins, as well as a hypothetical protein from *Lactobacillus casei*. The 3D structure profile, however, also detects a structural relationship between CRP and the cAMP dependent protein kinase family that the sequence profile does not. The 3D compatibility search is able to detect distant relationships, well below the level of 25% sequence identity, that are often difficult to detect by sequence similarity.

3. 3D Compatibility Search Based on Ribose Binding Protein from E.Coli 3D structure profiles confirm and extend proposals that the lac and related repressors have structures similar to those of ribose binding protein (RBP). RBP is a periplasmic protein involved in ribose transport. It is a member of a family of periplasmic binding proteins that have related folding patterns, yet little sequence similarity. Some sequence similarity has been noted between RBP, galactose binding protein (GBP), and arabinose binding protein (ABP), although ABP is the most dissimilar of the three. A sequence similarity between ABP and the lac and gal repressors has been described in the literature. Based on this sequence similarity and the known structure of ABP, a model of the sugar binding site of lac repressor has been proposed.

Figure 5A:
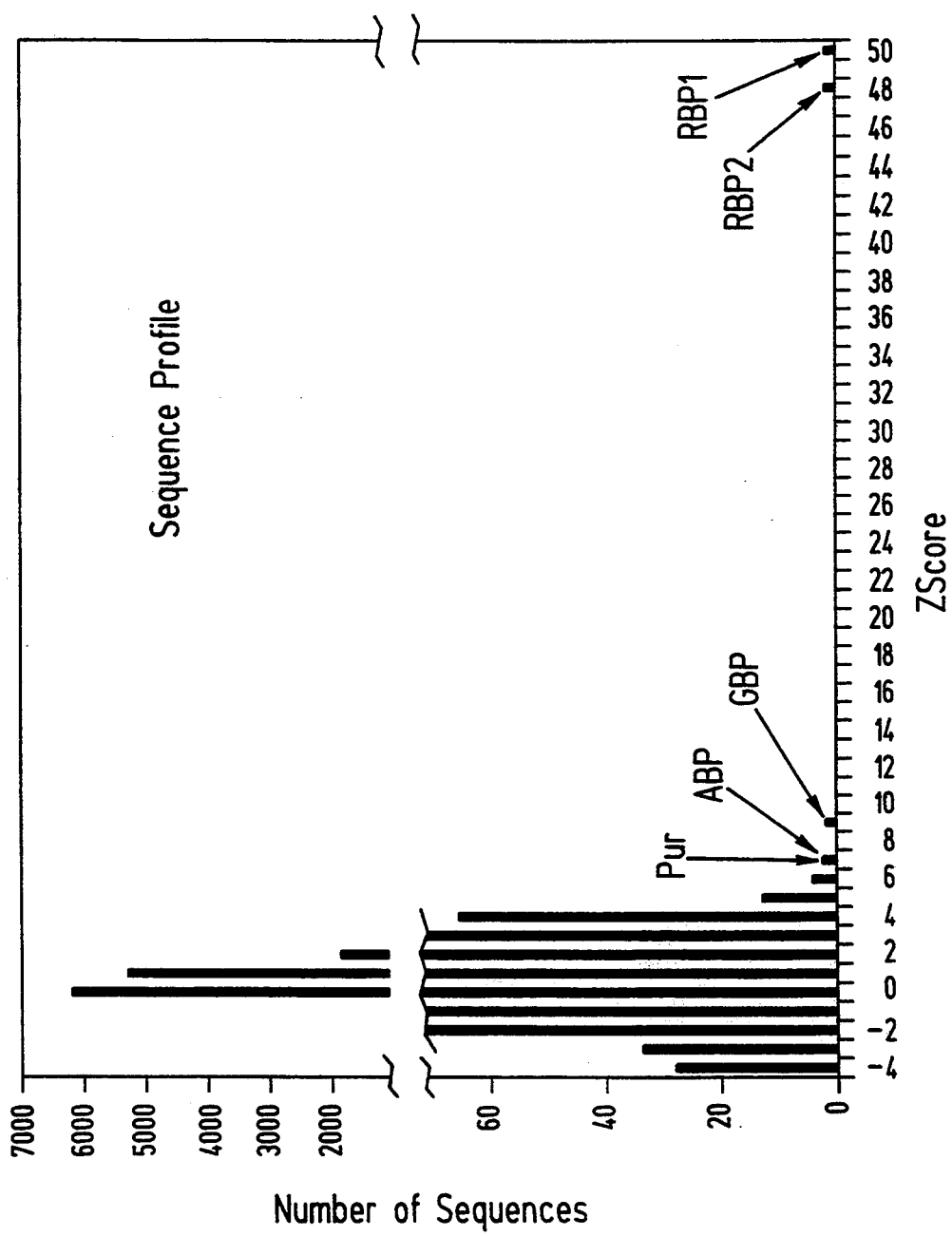
FIG. 5a is a graph showing the results of a prior art sequence homology search using a sequence profile constructed from the E. Coli ribose binding protein.

FIG. 5a summarizes a sequence homology search using a prior art sequence profile constructed from the *E. coil* RBP sequence. The bar graph shows the number of sequences that give a particular ZScore. A gap opening penalty of 45 and a gap extension penalty of 0.05 were used. The top scoring proteins labeled in the figure are RBP1 (*E. coil* ribose binding protein precursor, ZScore=49.0), RBP2 (*S. typhimurium* ribose binding protein precursor, ZScore=49.0), RBP2 (*S. typhimurium* ribose binding protein precursor, ZScore=47.9), GBP (*E. coli* galactose binding protein, ZScore=8.0), Pur (*E. coli* pur repressor, ZScore=6.1), and ABP (*E. coli* arabinose binding protein, ZScore=6.0).

Figure 5B:
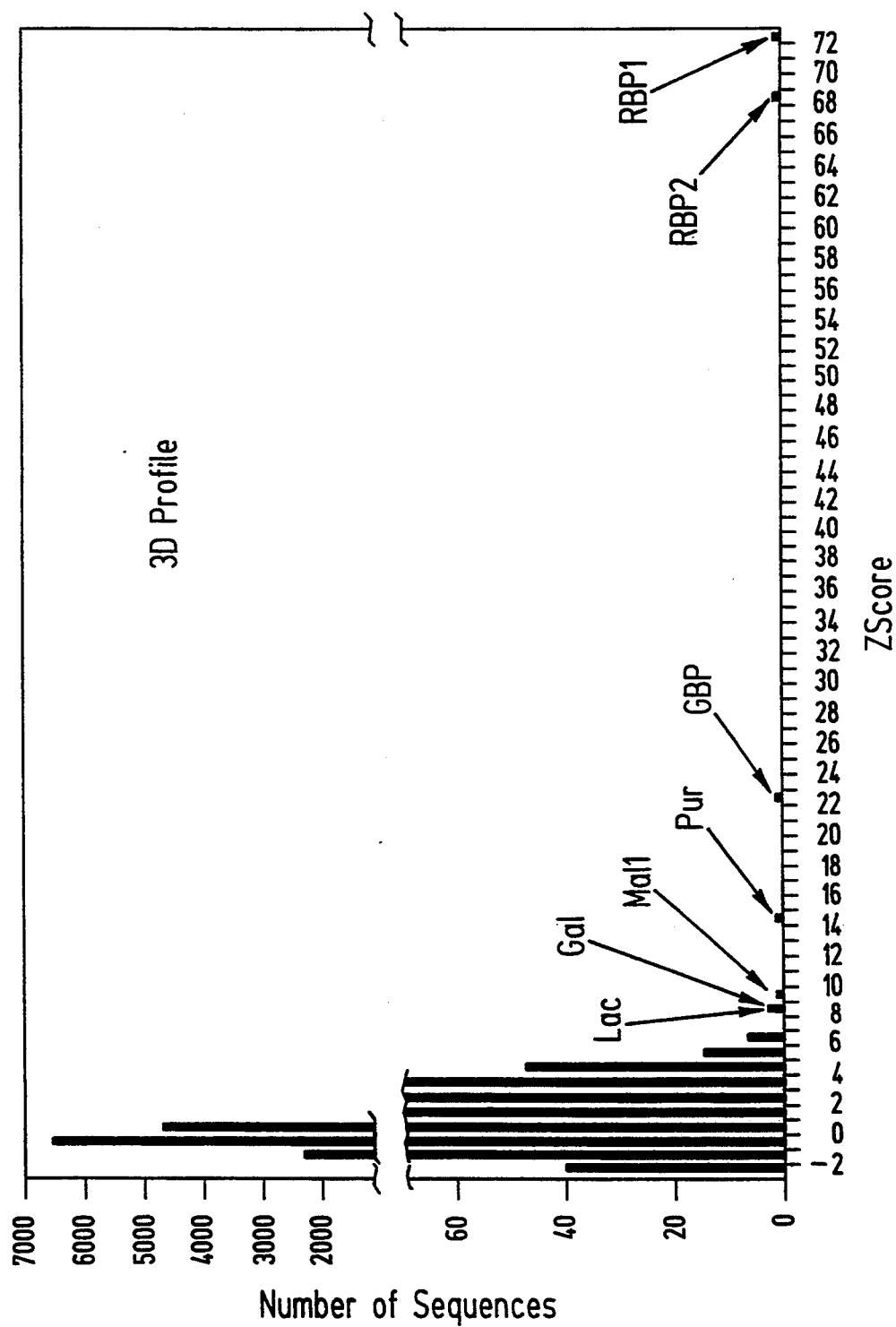
FIG. 5b is a graph showing the results of a structure compatibility search using a 3D structure profile constructed from the E. coli ribose binding protein structure, using the present invention.
Figure 8:
FIG. 8 is Table III, representing top scoring proteins derived from a 3D structure profile and a 3D compatibility search.

FIG. 5b shows the results of a 3D compatibility search using a 3D structure profile constructed from the *E. coil* ribose binding protein structure in accordance with the present invention. The bar graph shows the number of sequences that give a particular ZScore. A gap opening penalty of 5.0 and a gap extension penalty of 0.2 were used. The top scoring proteins labeled in the figure are RBP1 (*E. coil* ribose binding protein precursor, ZScore=72.2), RBP2 (*S. typhimurium* ribose binding protein, ZScore=68.9), GBP (*E. coil* galactose binding protein, ZScore=22.2), Pur (*E. coil* pur repressor, ZScore=14.2), Mal (*E. coil* Mal1 protein, ZScore=9.0), Gal (*E. coil* gal repressor, ZScore=8.5), and Lac (*Klebsiella pneumoniae* lac repressor, ZScore=8.1).

The top scoring proteins in the sequence homology search are RBP and GBP. The next highest scoring protein is pur repressor, which is a member of the lac repressor family. On the basis of sequence similarity, however, the case for overall structural similarity between RBP and pur repressor is relatively weak. The Zscore using the sequence profile is in the range (below 7) where spurious relationships can occur.

The case for similar structures is greatly strengthened with a 3D compatibility search based on a 3D structure profile made from the RBP structure, as shown in FIG. 5b. The two highest scoring proteins are RBP and GBP, but the next highest scoring proteins are all members of the lac repressor family, all having quite significant ZScores (above 8). This suggests that the effector binding domains of these repressors indeed fold in a manner similar to RBP. ABP is not a high scoring protein, suggesting that the structures of the lac repressor family and RBP are more similar than the structures of ABP and RBP. Moreover, a 3D compatibility search using a 3D structure profile constructed from the ABP structure did not reveal a significant structural relationship between ABP and the repressor proteins (not shown). Thus, the RBP structure may prove to be a better model of the overall structure of the effector binding domains of the lac repressor family than the structure of ABP.

4. 3D Compatibility Search Using a 3D Structure Profile for Actin

In 1990, three-dimensional structures were reported for the N-terminal domain of the 70K bovine heat shock cognate protein HSC70 (K. M. Flaherty, C. DeLuca-Flaherty, D. B. McKay, *Nature*, 346, 623–628 (1990)) and for muscle actin in a complex with DNase I (W. Kabsch, H. G. Mannherz, D. Suck, E. F. Pai, K. C., Holmes, *Nature*, 347, 37–44 (1990)). The authors found "unexpected . . . almost perfect structural agreement" between the two structures, although there is virtually no sequence similarity. The similarity in structure in the absence of sequence similarity would seem to present a severe test of 3D structure profiles. Accordingly, a 3D structure profile was generated from the actin coordinates and a 3D compatibility search was performed. The top scoring proteins are listed in TABLE III. All sequences that received a ZScore of 6.0 or greater are listed.

Following the actin sequences (fgr is an actin-protein kinase fusion protein), the next four highest scoring protein sequences are all member of the 70K heat shock protein family, three of which have ZScores above 7. The bovine HSC70 protein, known to have a very similar structure to actin, received a ZScore of 6.99 and is shown in bold type in the table. Thus, the 3D compatibility search indicates a structural correspondence between actin and members of the 70K heat shock protein family, a result unobtainable by a sequence homology search.

Other Uses

While the discussion above has focussed on using the inventive method to compare a plurality of known sequences of unknown structure to a single 3D structure profile in order to identify those sequences most likely to have compatible structures, the invention may be used for other purposes as well. For example, a "library" comprising a plurality of 3D structure profiles may be generated so that a new sequence of unknown structure may be compared to each of the library members to identify the most compatible structure corresponding to the sequence.

A further use would be to create a library of 3D structure profiles for fragments of known protein structures. A new sequence of unknown structure may be compared to each of the library members to identify the most compatible structure fragments corresponding to subportions of the sequence. The 3D structure of the sequence may be inferred to be similar to the sum of the corresponding structure fragments. In this manner, the inventive method may be used to assign a protein sequence to a 3D structure when no previous example of the structure exists.

Another use of the inventive method that is of significance is verification of protein models. A problem in the determination of protein structure by x-ray crystallography or NMR is being certain that the final protein model is correct. At present, the main method of verification of an x-ray derived protein model is to compare the calculated x-ray pattern to the observed x-ray pattern (the R-factor). Verification of NMR models is a currently developing field. For many protein models determined from energy calculations, homology, or "inspired" guesswork, there is essentially no effective means of verification.

The present invention provides an effective method of verifying a protein model by generating a 3D structure profile from the coordinates of the model. The 3D structure profile is then compared to the protein sequence on which the model was based. Tests have shown that a correct model of a protein structure results in a 3D structure profile that compares closely to the protein sequence, generating a high ZScore. On the other hand, an incorrect model of the protein structure results in a 3D structure profile that does not compare as well with the protein sequence; the 3D structure profile does not recognize its "own" sequence with a significant ZScore.

Still another use of the invention is as a screening technique for determining protein sequences that have a structure similar or homologous to the structure of a known sequence. This screening can be done in at least two ways. First, if the 3D structure of a protein is known, the inventive method can be used to screen a library of known sequences to determine structural analogs to the protein, as described above. The analogs can then be tested, using known techniques, for a desired biological activity, such as inhibition or stimulation of a receptor. Examples of such inhibition or stimulation are those occurring between a growth factor or a cytokine and their cell-membrane cell-membrane receptors. Those of ordinary skill in the art will know of other protein-receptor relationships to which the inventive screening method can be applied.

Second, if the structure of a protein is not known, the inventive method can be used to compare the sequence of that protein to a library of 3D profiles representing known structures, as described above. Once a compatible 3D structure is determined (which itself is a structural analog to the original protein sequence), that structure can then be used to screen a library of known sequences to determine other structural analogs to the original protein sequence. As described above, the analogs can then be tested for biological function, such as their ability to stimulate or inhibit the interaction between the original protein and a binding partner.

Yet another use of the invention is for building three-dimensional models for protein sequences that have a structure similar or homologous to the structure of a known sequence. A 3D structure profile is prepared form the known 3D structure. The profile is then used according to the inventive method to screen a library of known sequences to determine structural analogs to the original protein sequence, as described above. From the known 3D structure, the protein backbone of the analogs can be determined.

Conclusion

Prediction of protein structures from amino acid sequences requires a link between three-dimensional structures and one-dimensional sequences. In the inventive method, this link is provided by the reverse approach of converting a three-dimensional structure to a one-dimensional string of environmental classes. After this first step, the complexity of three-dimensional space is eliminated, but the 3D-1D relationship at the heart of the protein folding problem is preserved in the 3D structure profile. That related sequences can be detected by 3D structure profiles, which contain no direct information about amino acid type, might seem surprising. This suggests that the environmental classes based on area, polarity, and secondary structure are important parameters of folding.

To predict protein structures that are only distantly related to some known structure requires some way of simulating the malleability of real proteins. Distantly related proteins differ in the majority of their side-chains and also frequently differ in segments of backbone, particularly in loops that connect segments of secondary structures. 3D structure profiles simulate this malleability of proteins by using a statistical approach embodied in the 3D-1D table (TABLE I), and also in the dynamic programming algorithm. In particular, the tolerance of local unfavorable amino acid pairings and insertions and deletions in the alignments introduce considerable flexibility. These features are carried over from the earlier sequence profile methods and more general database searching algorithms and permit the 3D structure profile to recognize sequences that are folded similarly, but not necessarily identically, to a known structure. Thus, the present invention marries two distinct lines in the study of proteins. One is the sequence comparison and database searching line, the other is that of conformational energy calculations and consideration of stereochemistry and packing. In a 3D structure profile, stereochemistry and energetics enter implicitly into the assignment of the environmental classes through the buried area of each residue and the polarity of atoms in the environment.

3D compatibility searches are able to detect structural relationships that may not be apparent by sequence similarity. Thus, 3D compatibility searches should provide a useful complement to sequence homology searches in attacking the inverse protein folding problem.

Summary

In summary, the preferred embodiment of the inventive method starts with a known three-dimensional protein structure P and determines three key features of each residue's environment within the structure: (1) the total area A of the residue's side-chain that is buried by other protein atoms, inaccessible to solvent; (2) the fraction f of the side-chain area that is covered by polar atoms (O, N) or water; and (3) the local secondary structure s.

Thereafter, each position corresponding to a residue is assigned to one of a plurality of environment classes, based upon the A, f, and s values for the residue, thereby generating a one-dimensional environment string E which represents the environment class of each residue in the folded protein structure. A 3D structure profile table T is created containing score values that represent the frequency of finding each of the 20 common amino acids from known protein structures at each position of the environment string E. Thereafter, using known search techniques, the method determines the most favorable alignment of a target protein sequence S to the residue positions defined by the environment string E, and determines a best fit score $S_{ij}$ from the structure profile table T. Thereafter, a ZScore may be determined for the target sequence relative to a group of tested target sequences.

A number of embodiments of the present invention have been described. Nevertheless, it will be understood that various modifications may be made without departing from the spirit and scope of the invention. For example, as noted above, a larger number of environmental classifications may be used to recognize finer distinctions in residue environments. Additionally, other structural parameters could be used to define the environment classes. As another example, other weighting functions may be used to determine particular values for the 3D-1D scores using in generating 3D structure profile tables. Further, a larger sample of known protein structures could be used to generate the statistical data from which such 3D-1D scores are determined. Also, 3D-1D scores can be calculated directly from the 3D protein environment structural parameters (e.g., A, f, and s), eliminating the need to assign each residue position to a discrete environmental class. Accordingly, it is to be understood that the invention is not to be limited by the specific illustrated embodiment, but only by the scope of the appended claims.

We claim:

1. A computer-assisted method for characterizing the three-dimensional structure of a protein, using a programmed computer comprising a processor, a data storage system, at least one input device, and at least one output device, comprising the steps of:
   (a) generating input data for the programmed computer, including the steps of:
      (1) determining, from the three-dimensional structure of the protein, values for n structural properties $P_1, P_2, \ldots P_n$ for each amino acid residue position of the protein;
      (2) assigning each residue of the protein to one of a plurality of environment classes, based upon the values for the n structural properties $P_1, P_2, \ldots P_n$ for the residue, thereby generating a one-dimensional environment string comprising the environment class of each residue in the three-dimensional protein structure;
   (b) inputting the generated input data into the programmed computer through one of the input devices;
   (c) comparing, by means of the processor, the environment string to a computer database of other proteins of known three-dimensional structure stored in the computer data storage system;
   (d) selecting, using computer methods, analogous three-dimensional protein structures in the computer database;
   (e) outputting to at least one output device the selected analogous three-dimensional protein structures.

2. A computer-assisted method for characterizing the three-dimensional structure of a protein, using a programmed computer comprising a processor, a data storage system, at least one input device, and at least one output device, comprising the steps of:
   (a) generating input data for the programmed computer, including the steps of:
      (1) determining the total area A of the side-chain of each residue of the protein that is buried by other atoms of the protein, inaccessible to solvent;
      (2) determining the fraction f of the side-chain area of each residue of the protein that is covered by polar atoms or water; and
      (3) determining the local secondary structure s of each residue of the protein;
   (b) inputting the generated input data into the programmed computer through one of the input devices;
   (c) comparing, by means of the processor, the A,f, and s values for each residue to a computer database of other proteins of known three-dimensional structure stored in the computer data storage system;
   (d) selecting, using computer methods, analogous three-dimensional protein structures in the computer database;
   (e) outputting to at least one output device the selected analogous three-dimensional protein structures.

3. A computer-assisted method for characterizing the three-dimensional structure of a protein, using a programmed computer comprising a processor, a data storage system, at least one input device, and at least one output device, comprising the steps of:
   (a) generating input data for the programmed computer, including the steps of:
      (1) determining the total area A of the side-chain of each residue of the protein that is buried by other atoms of the protein, inaccessible to solvent;
      (2) determining the fraction f of the side-chain area of each residue of the protein that is covered by polar atoms or water;
      (3) determining the local secondary structure s of each residue of the protein;
      (4) assigning each residue of the protein to one of a plurality of environment classes, based upon the A, f, and s values for the residue, thereby generating a one-dimensional environment string comprising the environment class of each residue in the three-dimensional protein structure;
   (b) inputting the generated input data into the programmed computer through one of the input devices;
   (c) comparing, by means of the processor, the environment string to a computer database of other proteins of known three-dimensional structure stored in the computer data storage system;
   (d) selecting, using computer methods, analogous three-dimensional protein structures in the computer database;
   (e) outputting to at least one output device, the selected analogous three-dimensional protein structures.

4. The method of claim 3, wherein the plurality of environment classes is determined in part by combining the range of A and f values for the residue to determine discrete value regions, each value region comprising at least part of an environment class.

5. The method of claim 4, wherein the plurality of environment classes is determined by combining the determined discrete value regions with the range of s values.

6. A computer-assisted method for characterizing the frequency of occurrence of each of 20 common amino acid residues within a plurality of environment classes, comprising the steps of:
   a. generating, using computer methods, a computer database table having one column comprising a plurality of environment class values, and a plurality of columns, one for each of 20 common amino acid residues, each of the plurality of columns comprising a plurality of frequency values derived from known protein sequences having known three-dimensional structures, each frequency value corresponding to one of the plurality of environment class values.

7. The method of claim 6, wherein the frequency value for each amino acid residue i corresponding to an environment class value j is determined from the formula:

$$\text{Value } ij = \ln\left(\frac{P(i,j)}{Pi}\right)$$

where P(ij) is the probability of finding amino acid residue i in environment class j, and Pi is the overall probability of finding amino acid residue i in any environment class.

8. The method of claim 6, wherein the environment class values are deterined by the steps of:
   a. determining the total area A of the side-chain of each residue of each known protein sequence that is buried by other atoms of the protein, inaccessible to solvent;
   b. determining the fraction f of the side-chain area of each residue of each such protein that is covered by polar atoms or water;
   c. determining the local secondary structure s of each residue of each such protein;
   d. combining the range of A and f values for each residue to determine discrete value regions;
   e. combining the determined discrete value regions with the range of s values.

9. The method of claim 8, wherein the size of each value region is adjusted iteratively to maximize the total frequency value summed over all amino acid residues of the known protein sequence in accordance with the formula:

$$\text{Total } 3D\text{-}1D \text{ Score} = \sum_{ij} N_{ij}\ln\left(\frac{P(i,j)}{Pi}\right)$$

where P(ij) is the probability of finding amino acid residue i in environment class j, Pi is the overall probability of finding amino acid residue i in any environment class, and $N_{ij}$ is the number of amino acid residues i in environment class j.

10. A computer-assisted method of generating a profile table characterizing the three-dimensional structure of a protein, using a programmed computer comprising a processor, a data storage system, at least one input device, and at least one output device, comprising the steps of:
   (a) generating input data for the programmed computer, including the steps of:
      (1) determining, from the three-dimensional structure of the protein, values for n structural properties $P_1, P_2, \ldots P_n$ for each amino acid residue position of the protein;
      (2) generating, using computer methods, a table having a plurality of columns, one for each of 20 common amino acid residues, and as many rows as there are amino acid residue positions in the protein being characterized, each table entry being a frequency value derived from known protein sequences having known three-dimensional structures, each frequency value being the frequency of occurrence of the structural properties $P_1, P_2, \ldots P_n$ of each amino acid residue of the known protein sequences corresponding to each amino acid residue of the protein being characterized;
   (b) inputting the generated input data into the programmed computer through one of the input devices;
   (c) selecting, using computer methods, from the table information analogous three-dimensional protein structures of the protein being characterized;
   (d) outputting to at least one output device the selected analogous three-dimensional protein structures.

11. The method of claim 10, wherein each frequency value is determined as a score S(a) for each amino acid residue type a in the three-dimensional protein structure from the values for the structural properties $P_1, P_2, \ldots P_n$ in accordance with the following equation:

$$S(a) = c_1(a)P_1 + c_2(a)P_2 + \ldots c_n(a)P_n$$

where $c_1(a), c_2(a), \ldots c_n(a)$ are empirically determined constants.

12. A computer-assisted method of comparing a known three-dimensional protein structure to a known protein sequence having an unknown three-dimensional structure, in order to determine compatibility of the structure of the protein sequence with the known protein structure, using a programmed computer comprising a processor, a data storage system, at least one input device, and at least one output device, comprising the steps of:
   (a) generating input data for the programmed computer, including the steps of:
      (1) generating, using computer methods, a three-dimensional structure profile table characterizing the three-dimensional structure of the known protein by the method of claim 10;
      (2) comparing, using computer methods, the protein sequence to the three-dimensional structure profile table to determine the most favorable alignment of the protein sequence to the environment string stored in the computer data storage system;
   (b) inputting the generated input data into the programmed computer through one of the input devices;
   (c) selecting, using computer methods, the most favorable alignment indicative of the compatibility of the structure of the protein sequence with the known protein structure;
   (d) outputting to at least one output device the selected analogous three-dimensional protein structures.

13. A computer-assisted method of generating a profile table characterizing the three-dimensional structure of a protein, using a programmed computer comprising a processor, a data storage system, at least one input device, and at least one output device. comprising the steps of:
   (a) generating input data for the programmed computer, including the steps of:
      (1) determining the total area A of the side-chain of each residue of the protein that is buried by other atoms of the protein, inaccessible to solvent;
      (2) determining the fraction of the side-chain area of each residue of the protein that is covered by polar atoms or water;
      (3) determining the local secondary structure s of each residue of the protein;
      (4) assigning each residue of the protein to one of a plurality of environment classes, based upon the A, f, and s values for the residue, thereby generating a one-dimensional environment string comprising the environment class of each residue in the three-dimensional protein structure;

(5) generating using computer methods, a table having one column comprising the generated environment string, and a plurality of columns, one for each of 20 common amino acid residues, each of the plurality of columns comprising: a plurality of frequency values derived from known protein sequences having known three-dimensional structures, each frequency value comprising the frequency of occurrence of the corresponding amino acid residue in the corresponding environment class of the environment string;

(b) inputting the generated input data into the programmed computer through one of the input devices:

(c) selecting, using computer methods, from the table information analogous three-dimensional protein structures of the protein being characterized;

(d) outputting to at least one output device the selected analogous three-dimensional protein structures.

14. A computer-assisted method of comparing a known three-dimensional protein structure with a known protein sequence having an unknown three-dimensional structure, in order to determine compatibility of the structure of the protein sequence with the known protein structure, using a programmed computer comprising a processor, a data storage system, at least one input device, and at least one output device, comprising the steps of:

(a) generating input data for the programmed computer, including the steps of:

(1) generating, using computer methods, a three-dimensional structure profile table characterizing the three-dimensional structure of the known protein by means of a one-dimensional environment string;

(2) comparing, using computer methods, the protein sequence to the three-dimensional structure profile table to determine the most favorable alignment of the protein sequence to the environment string;

(b) inputting the generated input data into the programmed computer through one of the input devices;

(c) selecting, using computer methods, the most favorable alignment indicative of the compatibility of the structure of the protein sequence with the known protein structure;

(d) outputting to at least one output device the selected analogous three-dimensional protein structures.

15. The method of claim 14, wherein the step of generating the three-dimensional structure profile table comprises the steps of:

a. determining the total area A of the side-chain of each amino acid residue of the known protein structure that is buried by other atoms of the protein, inaccessible to solvent;

b. determining the fraction f of the side-chain area of each amino acid residue of the known protein structure that is covered by polar atoms or water;

c. determining the local secondary structure s of each amino acid residue of the known protein structure;

d. assigning each amino acid residue of the known protein structure to one of a plurality of environment classes, based upon the A, f, and s values for the amino acid residue, thereby generating a one-dimensional environment string comprising the environment class of each amino acid residue in the known three-dimensional protein structure;

e. generating, using computer methods, a table having one column comprising the generated environment string, and a plurality of columns, one for each of 20 common amino acid residues, each of the plurality of columns comprising a plurality of frequency values derived from known protein sequences having known three-dimensional structures, each frequency value comprising the frequency of occurrence of the corresponding amino acid residue in the corresponding environment class of the environment string.

16. The method of claim 14, wherein the step of comparing the protein sequence to the three-dimensional structure profile table accounts for insertions and deletions of amino acid residues in the protein sequence.

17. The method of claim 16, wherein the step of comparing the protein sequence to the three-dimensional structure profile table includes computing $S_{ij}$ as the score for the most favorable alignment in accordance with the formula:

$$S_{ij} = \text{Profile}(j, \text{column}_{a_i}) + \max \begin{bmatrix} S_{i-1,j-1}, \\ \max_{2 \leq k \leq j-1}(S_{i-1,j-k} - w_k), \\ \max_{2 \leq l \leq i-1}(S_{i-1,j-1} - w_l) \end{bmatrix}$$

where $S_{ij}$ is the score for the alignment of the protein sequence with the three-dimensional structure profile table such that position i of the protein sequence is aligned with row j of the three-dimensional structure profile table, and $w_k$ and $w_l$ are given by:

$$w_k = p_{open}(j-k) \cdot m_{open} + \sum_{j=j-k}^{j-2} p_{extend}(j) \cdot m_{extend}$$

$$w_l = p_{open}(j-1) \cdot m_{open} + (l-1) \cdot p_{extend}(j-1) \cdot m_{extend}$$

with $m_{open}$ and $m_{extend}$ being global penalty multipliers corresponding to each amino acid residue represented by the environment string in the three-dimensional structure profile table, and $p_{open}$ and $p_{extend}$ being position-specific gap-opening and gap-extension penalties corresponding to each amino acid residue represented by the environment string in the three-dimensional structure profile table.

18. The method of claim 14, wherein a plurality of known protein sequences having an unknown three-dimensional structure are compared to the known three-dimensional protein structure, in order to determine compatibility of the structures of the plurality of protein sequences with the known protein structure.

19. The method of claim 14, wherein a known protein sequence having an unknown three-dimensional structure is compared to a plurality of known three-dimensional protein structures, in order to determine compatibility of the structure of the protein sequence with the plurality of known protein structures.

20. The method of claim 19, wherein the plurality of known three-dimensional protein structures comprises fragments of whole protein structures.

21. The method of claim 20, wherein a known protein sequence having a suspected three-dimensional structure is compared to the suspected three-dimensional protein structure, in order to determine compatibility of the suspected protein structure with the actual structure of the protein sequence.

22. A method for screening structural analogs of a known protein sequence having an unknown three-dimensional structure, using a programmed computer comprising a processor, a data storage system, at least one input device, and at least one output device, comprising the steps of:
  (a) generating input data for the programmed computer, including the steps of:
    (1) providing at least one known three-dimensional protein structure;
    (2) for each of the known protein structures, generating a three-dimensional structure profile table characterizing the three-dimensional structure of the known protein by means of a one-dimensional environment string;
  (b) inputting the generated input data into the programmed computer through one of input devices;
  (c) comparing, using computer methods, the protein sequence to each of the three-dimensional structure profile tables to determine the most favorable alignment of the protein sequence to each environment string stored in the computer data storage system;
  (d) generating, by means of the processor a score from each of the most favorable alignments indicative of the compatibility of the structure of the protein sequence with the corresponding known protein structure stored in the computer data storage system;
  (e) selecting, using computer methods, at least one of the known protein structures having a high score as a structural analog to the protein sequence;
  (f) outputting to at least one output device the selected analogous three-dimensional protein structures.

23. The method of claim 22, including the further steps of:
  a. using one of the selected known protein structures, generating a three-dimensional structure profile table characterizing the three-dimensional structure of the selected known protein by means of a one-dimensional environment string;
  b. comparing, using computer methods, a plurality of other known protein sequences having an unknown three-dimensional structure to the three-dimensional structure profile table to determine the most favorable alignment of each of the other protein sequences to the environment string;
  c. generating a score from each of the most favorable alignments indicative of the compatibility of the structure of each of the other protein sequences with the selected known protein structure;
  d. selecting, using computer methods, at least one of the other protein sequences having a high score as a structural analog to the original known protein sequence.

24. A method for screening structural analogs of a known protein sequence having a known three-dimensional structure, using a programmed computer comprising a processor, a data storage system, at least one input device, and at least one output device, comprising the steps of:
  (a) generating input data for the programmed computer, including the steps of:
    (1) generating a three-dimensional structure profile table characterizing the three-dimensional structure of the known protein by means of a one-dimensional environment string;
    (2) comparing, using computer methods, a plurality of other known protein sequence having an unknown three-dimensional structure to the three-dimensional structure profile table to determine the most favorable alignment of each of the other protein sequences to the environment string stored in the computer data storage system;
  (b) inputting the generated input data into the programmed computer through one of the input devices;
  (c) generating, by means of the processor, a score from each of the most favorable alignments indicative of the compatibility of the structure of each of the other protein sequences with the known protein structure;
  d. selecting, using computer methods, at least one of the other protein sequences having a high score as a structural analog to the original known protein sequence;
  (e) outputting to at least one output device the selected analogous three-dimensional protein structures.

25. A method for characterizing the three-dimensional structure of a protein, using a programmed computer comprising a processor, a data storage system, at least one input device, and at least one output device. comprising the steps of:
  (a) generating input data for the programmed computer, including the steps of:
    (1) determining, from the three-dimensional structure of the protein, values for n structural properties $P_1, P_2, \ldots P_n$ for each amino acid residue position of the protein;
    (2) assigning each residue of the protein to one of a plurality of environment classes, based upon the values for the n structural properties $P_1, P_2, \ldots P_n$ for the residue, thereby generating a one-dimensional environment string comprising the environment class of each residue in the three-dimensional protein structure;
  (b) inputting the generated input data into the programmed computer through one of the input devices;
  (c) selecting, using computer methods and the environment string, the probable three-dimensional structure of the protein from a computer database of other proteins of known three-dimensional structure;
  (d) outputting to at least one output device the selected analogous three-dimensional protein structures.

26. A method for characterizing the three-dimensional structure of a protein, using a programmed computer comprising a processor, a data storage system, at least one input device, and at least one output device. comprising the steps of:
  (a) generating input data for the programmed computer, including the steps of:
    (1) determining, from the three-dimensional structure of the protein, values for n structural properties $P_1, P_2, \ldots P_n$ for each amino acid residue position of the protein;

(2) assigning each residue of the protein to one of a plurality of environment classes, based upon the values for the n structural properties $P_1, P_2, \ldots P_n$ for the residue, thereby generating a one-dimensional environment string comprising the environment class of each residue in the three-dimensional protein structure;

(b) inputting the generated input data into the programmed computer through one of the input devices;

(c) selecting, using computer methods and the environment string, analogous three-dimensional protein structures from a computer database of other proteins of known three-dimensional structure;

(d) outputting to at least one output device the selected analogous three-dimensional protein structures.

* * * * *

UNITED STATES PATENT AND TRADEMARK OFFICE
CERTIFICATE OF CORRECTION

PATENT NO.: 5,436,850

DATED: Jul. 25, 1995

INVENTOR(S): Eisenberg, et al

It is certified that error appears in the above-identified patent and that said Letters Patent is hereby corrected as shown below:

In column 1, at line 8, please insert the following paragraph:

--This invention was made with Government support under Grant Nos. GM31299 and GM39558, awarded by the National Institutes of Health. The Government has certain rights in this invention.--

Signed and Sealed this

Twenty-third Day of February, 1999

Attest:

Q. TODD DICKINSON

*Attesting Officer*    *Acting Commissioner of Patents and Trademarks*